(12) United States Patent
Zhang et al.

(10) Patent No.: US 10,349,846 B2
(45) Date of Patent: Jul. 16, 2019

(54) PHOTOELECTRIC SENSOR, PHOTOELECTRIC MEASUREMENT METHOD AND HEART RATE MEASUREMENT EQUIPMENT

(71) Applicant: Silergy Semiconductor Technology (Hangzhou) LTD, Hangzhou, ZheJiang Province (CN)

(72) Inventors: Baoyu Zhang, Hangzhou (CN); Huisen He, Hangzhou (CN); Lili Shao, Hangzhou (CN); Yanni Zhang, Hangzhou (CN)

(73) Assignee: Silergy Semiconductor Technology (Hangzhou) LTD, Hangzhou (CN)

( * ) Notice: Subject to any disclaimer, the term of this patent is extended or adjusted under 35 U.S.C. 154(b) by 108 days.

(21) Appl. No.: 15/477,024

(22) Filed: Apr. 1, 2017

(65) Prior Publication Data
US 2017/0296074 A1 Oct. 19, 2017

(30) Foreign Application Priority Data
Apr. 19, 2016 (CN) .......................... 2016 1 0247159

(51) Int. Cl.
| | | |
|---|---|---|
| *A61B 5/02* | (2006.01) |
| *A61B 5/024* | (2006.01) |
| *A61B 5/22* | (2006.01) |
| *A61B 5/00* | (2006.01) |
| *G01V 8/14* | (2006.01) |
| *H03K 17/78* | (2006.01) |
| *G16H 40/63* | (2018.01) |
| *G06F 19/00* | (2018.01) |

(52) U.S. Cl.
CPC .......... *A61B 5/02416* (2013.01); *A61B 5/222* (2013.01); *A61B 5/6869* (2013.01); *G01V 8/14* (2013.01); *G06F 19/00* (2013.01); *G16H 40/63* (2018.01); *H03K 17/78* (2013.01)

(58) Field of Classification Search
CPC ... A61B 5/02416; A61B 5/222; A61B 5/6869; G06F 19/00; G16H 40/63; G01V 8/14; H03K 17/78
See application file for complete search history.

(56) References Cited

U.S. PATENT DOCUMENTS

| | | |
|---|---|---|
| 6,987,258 B2 | 1/2006 | Mates |
| 7,244,919 B2 | 7/2007 | Ishikawa et al. |

(Continued)

*Primary Examiner* — Tony Ko
(74) *Attorney, Agent, or Firm* — Michael C. Stephens, Jr.

(57) ABSTRACT

A photoelectric sensor can include: a lighting element configured to generate a first optical signal, where a second optical signal is generated by reflection of the first optical signal when emitting an object; a driving circuit configured to drive the lighting element; a photoelectric conversion circuit configured to generate a first optical current in accordance with the second optical signal; and a programmable current amplifier circuit configured to sample and hold the first optical current when the lighting element is in operation, and to generate a second optical current when the lighting element is out of operation in one detection period, where the second optical current lasts for at least one working period in the detection period, and where the second optical current represents the first optical current.

20 Claims, 5 Drawing Sheets

(56) References Cited

U.S. PATENT DOCUMENTS

| | | | |
|---|---|---|---|
| 7,468,036 B1 * | 12/2008 | Rulkov | A61B 5/02438 600/485 |
| 8,097,840 B2 | 1/2012 | Zheng et al. | |
| 9,385,667 B2 | 7/2016 | Lichtenegger et al. | |
| 2004/0027471 A1 * | 2/2004 | Koseki | H04N 5/2173 348/300 |

* cited by examiner

PHOTOELECTRIC SENSOR, PHOTOELECTRIC MEASUREMENT METHOD AND HEART RATE MEASUREMENT EQUIPMENT

RELATED APPLICATIONS

This application claims the benefit of Chinese Patent Application No. 201610247159.2, filed on Apr. 19, 2016, which is incorporated herein by reference in its entirety.

FIELD OF THE INVENTION

The present invention generally relates to the field of sensors, and more particularly to photoelectric sensors, measurement methods, and heart rate measurement equipment.

BACKGROUND

A photo sensor is a sensor that uses a photo element as a detection element. The photo sensor may initially convert measured changes into optical signal changes, and then convert the optical signal to an electric signal by the photo element. Photo sensors are widely used in heart rate detectors. A heart rate detector can detect a person's heart rate, such that people can determine their own health status based on the detected heart rate. Systole and diastole of the heart causes blood to flow in the blood vessels, and the amount of blood flowing through the blood vessels correspond to different reflectivity. A heart rate detector may calculate the current heart rate by detecting fluctuations of the reflected light.

DETAILED DESCRIPTION

Reference may now be made in detail to particular embodiments of the invention, examples of which are illustrated in the accompanying drawings. While the invention may be described in conjunction with the preferred embodiments, it may be understood that they are not intended to limit the invention to these embodiments. On the contrary, the invention is intended to cover alternatives, modifications and equivalents that may be included within the spirit and scope of the invention as defined by the appended claims. Furthermore, in the following detailed description of the present invention, numerous specific details are set forth in order to provide a thorough understanding of the present invention. However, it may be readily apparent to one skilled in the art that the present invention may be practiced without these specific details. In other instances, well-known methods, procedures, processes, components, structures, and circuits have not been described in detail so as not to unnecessarily obscure aspects of the present invention.

When measuring a person's heart rate, a finger or wrist may be pressed against a chip of the heart rate measurement equipment. Light can be emitted to the vessels by a lighting element of the chip, and the density of light reflected from the finger or wrist may be measured by photoelectric converter. Photo-electrical current can be generated by the photoelectric converter, and the heart rate may be obtained by multiple measurements through conversion of the photo-electrical current by an analog-to-digital converter (ADC).

Heart rate measurement equipment is typically applied in portable equipment (e.g., bracelets, phones, smart watches, etc.), which can be powered by batteries and have accordant higher power loss requirements. Typically, most of the power losses are generated by driving the lighting element integrated in the chip. However, the density and time length of the emitting light of the lighting element determines the amplitude of the optical signal that is transferred to the photo-electrical converter. Therefore, the resolution of the variation of the amplitude may be limited to the resolution ratio of the ADC converter to influence the output of the sensor, and the density should be relatively strong and the time length should be relatively long, which can further increase power losses.

When the light reflected through the vessels of a finger or wrist is relatively weak, various approaches can be employed in order to improve the measurement accuracy. In one approach, the driving current of lighting element can be increased in order to make the lighting element emit stronger light. In another approach, the density of the light reflected through the vessels can be increased, or the number of the lighting elements can be increased, in order to make the photo-electrical converter receive stronger light. In yet another approach, the time length of the emitting light of the lighting element can be increased in the detection period. In still another approach, the sensing area of the photoelectric converter can be increased. However, power losses and/or chip size may be increased in such approaches, which can limit application in portable equipment.

In one embodiment, a photoelectric sensor can include: (i) a lighting element configured to generate a first optical signal, where a second optical signal is generated by reflection of the first optical signal when emitting an object; (ii) a driving circuit configured to drive the lighting element; (iii) a photoelectric conversion circuit configured to generate a first optical current in accordance with the second optical signal; and (iv) a programmable current amplifier circuit configured to sample and hold the first optical current when the lighting element is in operation, and to generate a second optical current when the lighting element is out of operation in one detection period, where the second optical current lasts for at least one working period in the detection period, and where the second optical current represents the first optical current.

Figure 1:
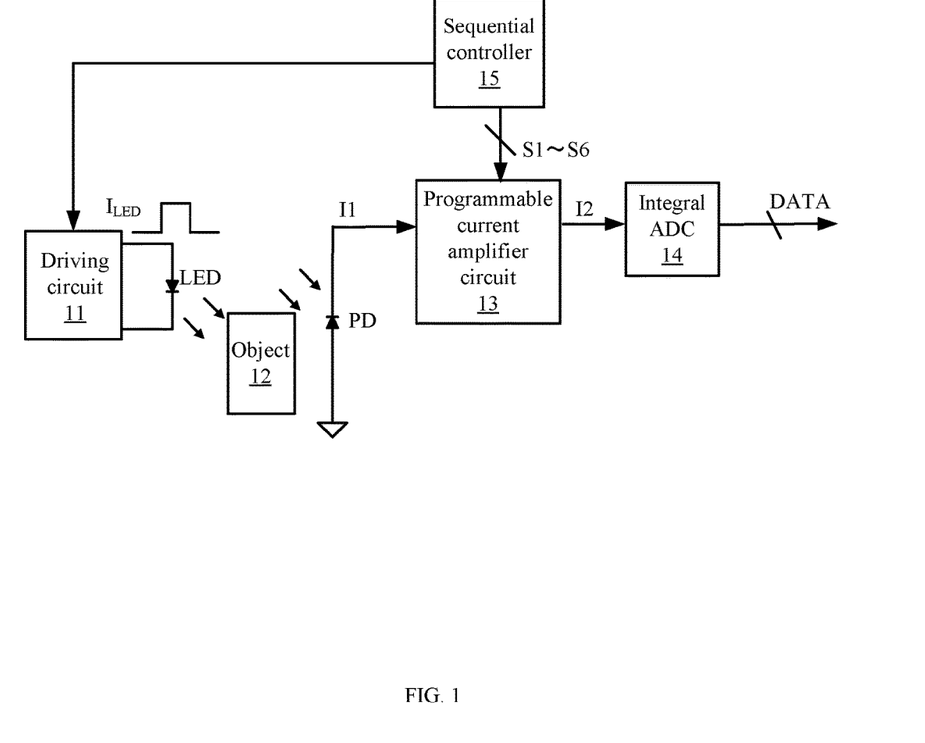
FIG. 1 is a schematic block diagram of an example photoelectric sensor, in accordance with embodiments of the present invention.

Referring now to FIG. 1, shown is a schematic block diagram of an example photoelectric sensor, in accordance with embodiments of the present invention. This particular example photoelectric sensor can include driving circuit 11, a lighting element (e.g., a light-emitting diode [LED], etc.), photoelectric converter (photodiode, etc.) PD, programmable current amplifier circuit 13, and integral type ADC 14. The LED can be driven by driving circuit 11 in order to generate optical signal L1. In this example, optical signal L1 can be a pulse type optical signal. The LED can be internal or external of the sensor, and the LED may be configured as monochromatic lighting diode. Optical signal L1 can be reflected by detected object 12 in order to generate detection light configured as optical signal L2.

Photodiode PD can convert received optical signal L2 to optical current I1. Because optical signal L1 can be a pulse type signal, optical signal L2 and optical current I1 may also be pulse type signals. Photodiode PD can thus convert the received optical signal into a current signal. Photodiode PD can be internal or external of the sensor. Programmable current amplifier circuit 13 can sample and hold optical current I1 when the LED is in operation, and may generate optical current I2 of one or more working periods when the LED is out of operation. Optical current I2 can represent the value of optical current I1. Also, the amplitude and/or pulse width of optical current I2 can be in direct proportion with that of optical current I1.

In one detection period, the LED may be driven by driving circuit 11 for at least one operation period. Optical signal L1 can include at least one pulse generated by the LED. Therefore, optical current I1 can include at least one pulse generated by photodiode PD. Optical signal L1 can be sampled by sampling and holding circuit of programmable current amplifier circuit 13 when optical signal L1 is generated by the LED. In addition, before the LED is out of operation, sampled optical current I1 may be held by the sampling and holding circuit (e.g., and 13). When the LED is out of operation, optical current I2 with an amplitude or pulse width in direct proportion with that of optical current I1 can be generated. In this way, greater power losses that might otherwise be generated by the continuous operation of LED can be substantially avoided during the detection time interval. Also, optical current I2 can be generated by programmable current amplifier circuit 13 when the LED is out of operation, and detection value DATA of the photoelectric sensor may be generated in accordance optical current I2.

Figure 2:
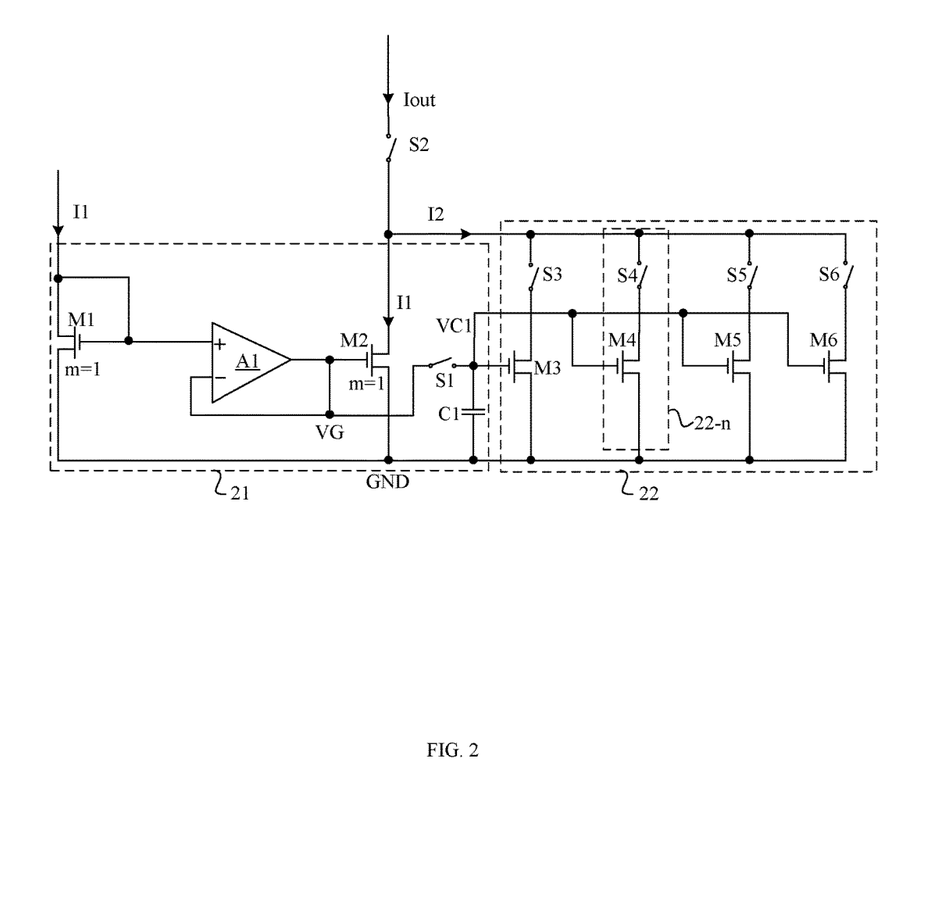
FIG. 2 is a schematic block diagram of an example programmable current amplifier circuit of a photoelectric sensor, in accordance with embodiments of the present invention.

Referring now to FIG. 2, shown is a schematic block diagram of an example programmable current amplifier circuit of a photoelectric sensor, in accordance with embodiments of the present invention. This particular example programmable can include sampling and holding circuit 21 and optical current generation circuit 22. Sampling and holding circuit 21 can sample and hold optical current I1 when the LED is in operation. For example, sampling and holding circuit 21 can include transistors M1 and M2, switch S1, capacitor C1, and operational amplifier A1.

Transistors M1 and M2 may form a current mirror configured as a cascade structure; however, other types of current mirror can also be utilized in certain embodiments. The gate electrodes of transistors M1 and M2 can be coupled to each other through operational amplifier A1. For example, the gate electrode of transistor M1 can connect to the non-inverting input terminal of operational amplifier A1. The inverting input terminal and the output terminal of operational amplifier A1 and gate electrode of transistor M2 can be connected. Therefore, due to the voltage following effect of the operational amplifier, the gate voltage of transistor M2 may follow that of transistor M1. Also, due to the isolation effect, the operation of post stage circuitry may not influence that of pre-stage circuitry. The drain electrode of transistor M1 can receive optical current I1, and due to the operation of the current mirror circuit that includes transistors M1 and M2, a current in the same proportion can be generated at the output of the current mirror circuit.

When operational amplifier A1 is not included in sampling and holding circuit 21, one terminal of switch S1 can be coupled to the common node between the gate electrodes of transistors M1 and M2. When operational amplifier A1 is included in sampling and holding circuit 21, one terminal of switch S1 can be coupled to the common node between the inverting input terminal of operational amplifier A1 and the gate electrode of transistor M2. The other terminal of switch S1 can connect to one terminal of capacitor C1, and the other terminal of capacitor C1 can connect to ground.

When the LED is driven in operation by driving circuit 11, optical current I1 can be generated by photo-electrical diode PD, and provided to programmable current amplifier circuit 13. In addition, switch S1 may be turned on, and the voltage across capacitor C1 can be equivalent with the gate voltages of transistors M1 and M2. Because transistors M1 and M2 operate in the linear mode and the source electrodes are coupled to ground, voltage VC1 across capacitor C1 equivalent with gate voltage VG can represent optical current I1. When the LED is out of operation, switch S1 may be turned off, and voltage VC1 across capacitor C1 can be maintained as gate voltage VG. Optical current generation circuit 22 can generate optical current I2 when the LED is out of operation. The amplitude or pulse width of optical current I2 can be in direct proportion with that of optical current I1.

Optical current generation circuit 22 can include several current units 22-$n$ coupled in parallel, each of which may include a switch and a transistor coupled in series. Each first terminal of current units 22-$n$ can be coupled together and configured as an output terminal of programmable current amplifier circuit 13, and each second terminal of current units 22-$n$ can be coupled to ground. The gate electrodes of the transistors of current units 22-$n$ can be coupled to the first terminal of capacitor C1. When the corresponding switch is turned on, the current of the present current unit may be provided to the output terminal of programmable current amplifier circuit 13. In addition, when the given switch is turned off, no current of the present current unit may be provided to the output terminal of programmable current amplifier circuit 13. Also, the amplitude of optical current I2 can be adjusted by controlling the switches of current units coupled in parallel to be on and off.

For example, size of transistor can be the same as that of transistor M2, and the size of switches of current units 22-$n$ may be in proportion (e.g., in sequence) with that of transistor M1. When driven by the same driving voltages, currents flowing through two transistors may be the same, indicating that the two transistors have the same sizes. When driven by same driving voltages, currents flowing through two transistors may be in proportion, indicating that the two transistors have proportional sizes. In one example, the sizes of switches of current units 22-$n$ can be arranged to be "m" power of 2 times of that of transistor M1, where "m" is natural number. For example, the size of transistor M3 may be the same as that of transistor M1. Also, the size of transistor M4 may be two times of that of transistor M1, and the size of transistor M5 can be 4 times of that of transistor M1, and so on. Because gate voltages of the transistors are all voltage VC1 across capacitor C1, the current of each current unit may be "m" powers of 2 times of optical current I1. Optical current I2 can be adjusted by controlling the on/off states of switches of current units 22-$n$.

In addition, the first terminal of switch S2 can connect to first terminal of each current unit, and the second terminal of switch S2 can be configured as the output terminal of programmable current amplifier circuit 13. The pulse width of optical current I2 may be adjusted by controlling the on/off states of switch S2. Regardless of whether the amplitude of optical current I2 is in proportion with that of optical current I1, pulse width of optical current I2 can be in proportion with that of optical current I1, or both the amplitude and pulse width of optical current I2 may be in proportion with that of optical current I1, and the average current of optical current I1 can be in proportion with that of optical current I1. Therefore, when the LED is out of operation, optical current I2 may represent optical current I1. Detection signal DATA can be generated in accordance with optical current I2 when the LED is out of operation, in order to decrease the power losses of driving circuit 11 and to improve working efficiency.

Integral ADC 14 can receive optical current I2, or to both optical currents I1 and I2, and may generate detection signal DATA as the output signal of the photoelectric sensor. For example, integral ADC 14 can be configured as a current ADC. As another example, optical current I2 can be converted to a voltage signal, and then processed by a voltage ADC. Furthermore, a current mirror circuit can be included and coupled between output terminal of photo-electrical diode PD and input terminal of programmable current amplifier circuit 13, and may isolate the interference to post stage circuitry by photo-electrical diode PD.

Furthermore, sequential controller 15 can be included to generate control signals to control the gain of programmable amplifier circuit 13, switches S1-S6, and driving circuit 11. For example, the pulse width of optical current I2 can be consistent with that of optical current I1, and the amplitude of optical current I2 can be adjusted in accordance with the current gain. The control signal of switch S2 may have a same frequency and duty cycle as the driving signal of driving circuit 11, in order to improve the current amplifying accuracy of programmable current amplifier circuit 13. Sampling and holding circuit 21 can sample and hold pulsed optical signal L1 when the LED is in operation. Optical current generation circuit 22 can generate optical current I2 when the LED is out of operation, and the amplitude and/or pulse width of optical current I2 can be in direct proportion with that of optical current I1. Therefore, no continuous operation of the LED may be needed in order to decrease power losses.

Figure 3:
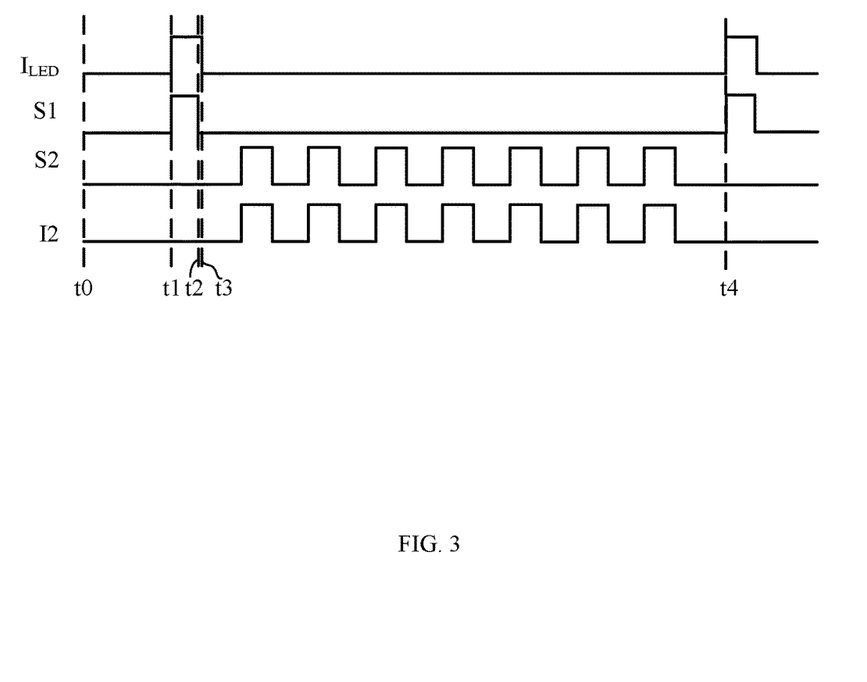
FIG. 3 is a waveform diagram of example operation of a photoelectric sensor, in accordance with embodiments of the present invention.

Referring now to FIG. 3, shown is a waveform diagram of example operation of a photoelectric sensor, in accordance with embodiments of the present invention. In time interval t0-t1, the LED may be out of operation and the system can be in a recovery state. Both of switches S1 and S2 can be turned off. As shown herein, $I_{LED}$ may represent the current flowing through the LED, and during time interval t1-t2, there may be a current flowing through the LED. Switch S1 can be turned on, and switch S2 may be turned off. Therefore, pulsed optical current I1 can be generated by photo electrical diode PD. In addition, programmable current amplifier circuit 13 can receive and sample and hold optical current I1. At moment t2, switch S1 can be turned off, and gate voltages of transistors M3, M4, M5, M6 may be consistent with that of transistor M1 at the moment of switch S1 being turned off. In time interval t2-t3, at moment t3, the LED may be out of operation, and both of switches S1 and S2 are turned off.

In time interval t3-t4, the LED may be out of operation, both of switches S1 and S2 may be turned off. The gate voltages of transistors M3, M4, M5, M6 can be consistent with that of transistor M1 at the moment of switch S1 being turned off. The on/off states of switch S2 can be controlled by sequential controller 15, and optical current I2 may be provided to integral ADC 14. For example, the amplitude of optical current I2 can be adjusted by the switching states of switches S3-S6 controlled by sequential controller 15 in accordance with the gain of programmable current amplifier circuit 13. Optical current I2 can be generated when the LED is out of operation, and may represent optical current I1. Detection signal DATA can be generated by integral ADC 14 in accordance with optical current I2, and may be configured as output signal of photoelectric sensor. The above operation can be repeated beginning at t4.

The average power loss of the LED in one detection period may be represented as below in Equation (1).

$$I_{LED\_AVG} = \frac{I_{LED} * (t_2 - t_1)}{t_4 - t_1} \quad (1)$$

In one detection period, only one pulsed optical current may be generated by the LED. The multiple pulsed optical current I2 provided to integral ADC 14 can be generated by programmable current amplifier circuit 13. In other approaches, in order to achieve same optical current I2 as described herein, the average power loss in one detection period of the LED may be represented as below in Equation (2).

$$I_{LED\_AVG1} = \frac{I_{LED} * (t_2 - t_1) * n}{t_4 - t_1} \quad (2)$$

For example, "n" can represent the number of pulses of optical current provided to integral ADC 14. For example, power losses of certain embodiments may only be 1/nth of that of other such approaches. Sampling and holding circuit 21 can sample and hold pulsed optical signal L1 when the LED is in operation. Optical current generation circuit 22 may generate optical current I2 when the LED is out of operation, and the amplitude and/or pulse width of which can be in direct proportion with that of optical current I1. Therefore, no continuous operation of the LED may be needed in order to decrease the power loss.

Figure 4:
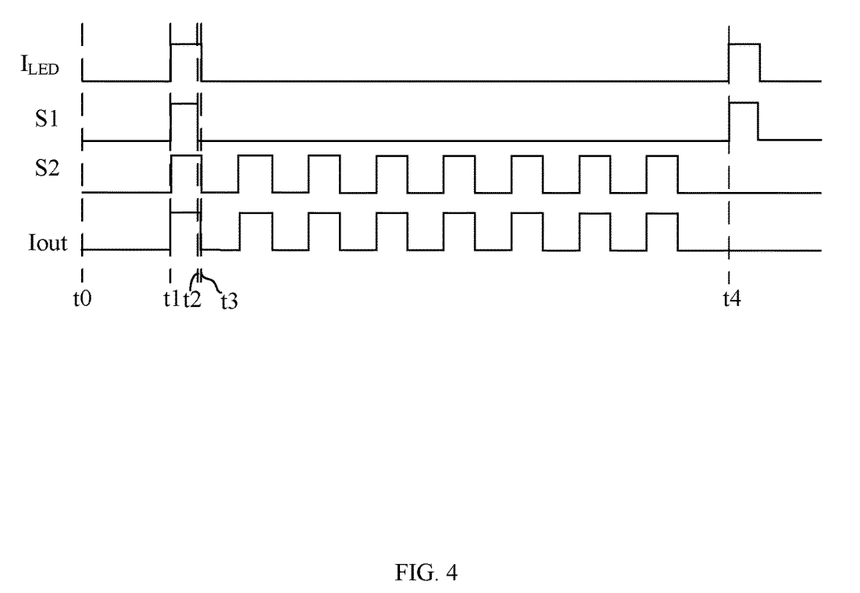
FIG. 4 is a waveform of another example operation of a photoelectric sensor, in accordance with embodiments of the present invention.

Referring now to FIG. 4, shown is a waveform of another example operation of a photoelectric sensor, in accordance with embodiments of the present invention. As distinguished from FIG. 3, in time interval t1-t3, switch S2 can be turned on. Therefore, when the LED is in operation and out of operation, optical currents I1 and I2 may both be provided to ADC 14, in order to improve the accuracy of photoelectric sensor. Sampling and holding circuit 21 can sample and hold pulsed optical signal L1 when the LED is in operation. Optical current generation circuit 22 may generate optical current I2 when the LED is out of operation, and the amplitude and/or pulse width of which can be in direct proportion with that of optical current I1. Therefore, no continuous operation of the LED may be needed in order to decrease the power loss.

In one embodiment, a method of photoelectric sensing can include: (i) generating, by a lighting element, a first optical signal; (ii) generating, by reflection of the first optical signal when emitting an object, a second optical signal; (iii) generating, by a photoelectric conversion circuit, a first optical current in accordance with the second optical signal; (iv) sampling and holding, by a programmable current amplifier circuit, the first optical current when the lighting element is in operation in one detection period; and (v) generating, by the programmable current amplifier circuit, a second optical current of at least one working period when the lighting element is out of operation, where the second optical current represents the first optical current.

Figure 5:
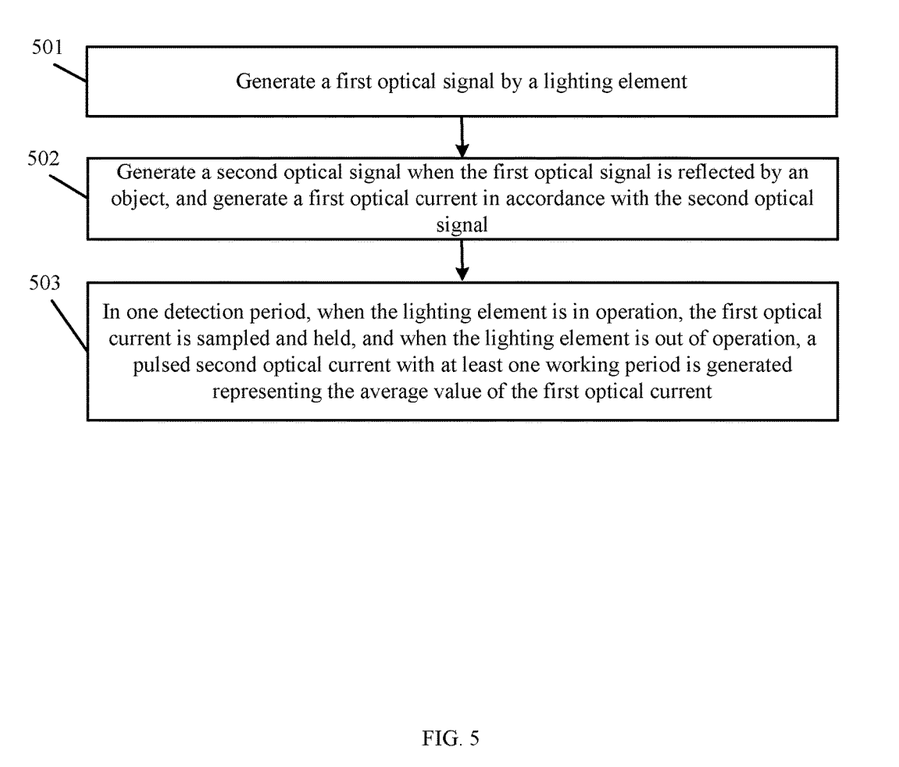
FIG. 5 is a flow diagram of an example method of photoelectric sensing, in accordance with embodiments of the present invention.

Referring now to FIG. 5, shown is a flow diagram of an example method of photoelectric sensing, in accordance with embodiments of the present invention. At 501, a first optical signal can be generated by a lighting element (e.g., an LED). At 502, a second optical signal can be generated when the first optical signal is reflected by an object (e.g., 12). Also, a first optical current (e.g., I1) can be generated in accordance with the second optical signal. At 503, in one detection period, when the lighting element is in operation, the first optical current can be sampled and held. When the lighting element is out of operation, a pulsed second optical current (e.g., I2) with at least one working period can be generated (e.g., by 13), representing the average value of the first optical current.

The optical currents can be pulsed optical current signals. In addition, the amplitude and/or pulse width of the second optical current can be in direct proportion with that of the first optical current. In one detection period, the lighting element can be in operation for at least one working period. Generation of the second optical current can include sampling and holding first optical current when the lighting element is in operation, and generating the second optical current in accordance with the first optical current when the lighting element is out of operation. The photoelectric sensing method can also include converting the second optical current to a detection signal by an ADC (e.g., 14) which can be configured as output signal.

In particular embodiments, the first optical current can be sampled and held when the lighting element is in operation, and a second optical current with an amplitude and/or pulse width in direct proportion with that of first optical current can be generated when the lighting element is out of operation. In this way, the lighting element may not be in a continuous operation during one detection period, which can reduce associated power losses, as compared to other approaches.

The embodiments were chosen and described in order to best explain the principles of the invention and its practical applications, to thereby enable others skilled in the art to best utilize the invention and various embodiments with modifications as are suited to particular use(s) contemplated. It is intended that the scope of the invention be defined by the claims appended hereto and their equivalents.

What is claimed is:

1. A photoelectric sensor, comprising:
   a) a lighting element configured to generate a first optical signal, wherein a second optical signal is generated by reflection of said first optical signal when emitting from an object;
   b) a driving circuit configured to drive said lighting element;
   c) a photoelectric conversion circuit configured to generate a first optical current in accordance with said second optical signal; and
   d) a programmable current amplifier circuit comprising a sampling and holding circuit configured to sample and hold said first optical current when said lighting element is in operation, an optical current generation circuit configured to generate a second optical current in accordance with said sampled and held first optical current when said lighting element is out of operation in one detection period, wherein said second optical current lasts for at least one working period in said detection period, wherein said second optical current represents said first optical current, wherein said sampling and holding circuit comprises a first switch coupled to said optical current generation circuit, and wherein said first switch is off when said lighting element is out of operation.

2. The photoelectric sensor of claim 1, wherein said first and second optical currents are pulsed optical current signals.

3. The photoelectric sensor of claim 2, wherein an amplitude of said second optical current is in direct proportion with an amplitude of said first optical current.

4. The photoelectric sensor of claim 2, wherein a pulse width of said second optical current is in direct proportion with a pulse width of said first optical current.

5. The photoelectric sensor of claim 1, wherein in one detection period, said lighting element is driven to be operated for at least one working period by said driving circuit.

6. The photoelectric sensor of claim 1, wherein said first switch is on when said lighting element is in operation.

7. The photoelectric sensor of claim 1, wherein said sampling and holding circuit comprises:
   a) first and second transistors configured as a current mirror circuit;
   b) said first switch having a first terminal coupled to a common node between said first and second transistors; and
   c) a first capacitor having a first terminal coupled to a second terminal of said first switch, and a second terminal coupled to ground.

8. The photoelectric sensor of claim 7, wherein:
   a) said optical current generation circuit comprises a plurality of current units coupled in parallel;
   b) each of said plurality of current units comprises a switch and a transistor coupled in series;
   c) gate electrodes of said transistors of said plurality of current units are coupled to said first terminal of said first capacitor; and
   d) a first terminal of each of said plurality of current units is coupled to output terminal of said programmable current amplifier circuit, and a second terminal of each of said plurality of current units is coupled to ground.

9. The photoelectric sensor of claim 8, wherein:
   a) each said first terminal of said plurality of current units is coupled to output terminal of said programmable current amplifier circuit through a second switch; and
   b) a pulse width of said second optical current is adjusted by controlling the on time of said second switch in each working period.

10. The photoelectric sensor of claim 8, wherein the size of each of said transistors of said plurality of current units is in direct proportion in sequence.

11. The photoelectric sensor of claim 1, further comprising an integral analog-to-digital converter (ADC) configured to convert said second optical current to a detection signal configured as an output signal of said photoelectric sensor.

12. The photoelectric sensor of claim 1, further comprising an integral ADC configured to convert said first and second optical currents to a detection signal configured as an output signal of said photoelectric sensor.

13. A heart rate measurement apparatus, comprising the photoelectric sensor of claim 1.

14. A method of photoelectric sensing, the method comprising: ##
   a) generating, by a lighting element, a first optical signal;
   b) generating, by reflection of said first optical signal when emitting an object, a second optical signal;

c) generating, by a photoelectric conversion circuit, a first optical current in accordance with said second optical signal;
d) sampling and holding, by a programmable current amplifier circuit comprising a sampling and holding circuit, said first optical current when said lighting element is in operation in one detection period;
e) generating, by an optical current generation circuit in said programmable current amplifier circuit, a second optical current in accordance with said sampled and held first optical current and being of at least one working period when said lighting element is out of operation, wherein said second optical current represents said first optical current, wherein said sampling and holding circuit comprises a first switch coupled to said optical current generation circuit, and wherein said first switch is off when said lighting element is out of operation.

15. The method of claim 14, wherein said first and second optical currents are pulsed optical current signals.

16. The method of claim 15, wherein an amplitude of said second optical current is in direct proportion with an amplitude of said first optical current.

17. The method of claim 15, wherein a pulse width of said second optical current is in direct proportion with a pulse width of said first optical current.

18. The method of claim 14, wherein in one detection period, said lighting element is driven to be operated for at least one working period by a driving circuit.

19. The method of claim 14, wherein said first switch is on when said lighting element is in operation.

20. The method of claim 14, further comprising converting said second optical current to a detection signal configured as an output signal.

* * * * *